United States Patent [19]

Skaggs et al.

[11] Patent Number: 4,992,256

[45] Date of Patent: Feb. 12, 1991

[54] PLAQUE DISCLOSING COMPOSITIONS

[75] Inventors: J. Michael Skaggs, New Brunswick; Robert E. Dickson, Bellmead; James H. Bowers, Somerville; Edward A. Tavss, Kendall Park, all of N.J.

[73] Assignee: Colgate-Palmolive Company, New York, N.Y.

[21] Appl. No.: 413,424

[22] Filed: Sep. 27, 1989

[51] Int. Cl.$^5$ .......................... A61K 7/16; A61K 9/68; A61K 9/12

[52] U.S. Cl. ...................................... 424/7.1; 424/440; 424/441; 424/45; 424/48; 428/49; 428/54; 428/58

[58] Field of Search .................................. 424/7.1, 49

[56] References Cited

U.S. PATENT DOCUMENTS

| | | | |
|---|---|---|---|
| 3,309,274 | 3/1967 | Brilliant | 167/84.5 |
| 3,624,219 | 11/1971 | Perlitsh | 424/7 |
| 3,903,252 | 9/1975 | Stearns et al. | 424/7 |
| 3,943,949 | 3/1976 | Ashton et al. | 132/89 |
| 3,997,658 | 12/1976 | Block et al. | 424/7 |
| 4,064,229 | 12/1977 | Block et al. | 424/7 |
| 4,302,439 | 11/1981 | Selwyn | 424/7 |
| 4,348,378 | 9/1982 | Kosti | 424/7 |
| 4,414,990 | 11/1983 | Yost | 132/91 |
| 4,431,628 | 2/1984 | Gaffar | 424/7.1 |
| 4,431,631 | 2/1984 | Clipper et al. | 424/53 |
| 4,444,746 | 4/1984 | Harvey et al. | 424/49 |
| 4,459,277 | 7/1984 | Kosti | 424/49 |
| 4,469,674 | 9/1984 | Shah et al. | 424/52 |
| 4,517,172 | 5/1985 | Southard | 424/7.1 |
| 4,590,061 | 5/1986 | Southard | 424/7.1 |
| 4,657,758 | 4/1987 | Goldemberg et al. | 424/49 |
| 4,666,700 | 5/1987 | Frysh | 424/7.1 |
| 4,666,708 | 5/1987 | Goldemberg et al. | 424/49 |
| 4,684,517 | 8/1987 | Clipper et al. | 424/52 |

FOREIGN PATENT DOCUMENTS

| | | |
|---|---|---|
| 05501 | 9/1987 | PCT Int'l Appl. . |
| 00463 | 1/1988 | PCT Int'l Appl. . |
| 2019215 | 1/1979 | United Kingdom . |
| 2135877 | 9/1984 | United Kingdom . |

Primary Examiner—Shep K. Rose
Attorney, Agent, or Firm—Robert L. Stone; Murray M. Grill

[57] ABSTRACT

Dental plaque-disclosing compositions comprising FD&C Red No. 40 which selectively stain plaque formed on tooth surfaces, making plaque easily observable to the naked eye at visible light wave-lengths.

11 Claims, No Drawings

PLAQUE DISCLOSING COMPOSITIONS

FIELD OF THE INVENTION

This invention relates to plaque disclosing compositions in the form of tablets, mouthrinses, dentifrices or aerosols containing F. D & C Red No.40 dye for use as a diagnostic tool and in the improvement of oral hygiene practices.

BACKGROUND OF THE INVENTION

Dental plaque, colonies of harmful bacteria which form on tooth surfaces and restorations, cannot be flushed away by simply rinsing with water. Active brushing of the teeth is required to remove the plaque which adheres to tooth surfaces It is a well accepted fact that dental plaque, when allowed to accumulate on tooth surfaces, can eventually lead to gingivitis, periodontal disease, caries and calculus. Thus, it is apparent that effective removal of deposits of dental plaque is absolutely essential for oral health. Accordingly, proper oral hygiene practices which may be carried out by an individual on his or her own teeth or by a dentist, would be facilitated by readily available means of identification and location of plaque deposits in the oral cavity.

Since dental plaque is usually transparent and colorless and not easily visible, an individual frequently is not aware of the quantity or the location of dental plaque present in the mouth. Therefore, it is desirable to use plaque-disclosing compositions to identify areas of the mouth where plaque buildup is a problem. The use of disclosing compositions motivates a person in the early removal of dental plaque by showing the presence and quantity of plaque.

Accordingly, dye indicators for dental plaque as a means of measuring tooth cleanliness and to affect proper oral hygiene practices, have been widely explored. A number of agents and techniques have been developed, some of which may be used conveniently and economically at home, whereas others may be used more effectively in a dental office.

Dyes effectively used at a dentist's office include the use of water-insoluble colorants in non-toxic carriers which can only be removed mechanically from the mouth, and fluorescent dyes which require application of a light source to be observable.

A disclosant dye must meet certain criteria in order to be useful as a plaque disclosing agent, particularly for home use. Firstly, the dye must be capable of adequately penetrating the plaque deposit, and stain said plaque so as to be readily visible to the user, without producing an excessively prolonged staining effect. This staining efficacy must be selective so as to identify the areas of plaque-formation on all tooth surfaces and not unduly stain gingival or other oral tissues. This selective staining efficacy must be coupled with easy removability from the mouth by simply washing or rinsing after use, i.e. it should be water-soluble. In addition, the taste must be pleasant and acceptable to the user, and the color must be pleasing. It must be harmless and non-toxic. Further, it should be visible under normal light conditions, not dependent on fluorescence excitation sources.

It is evident that certain previously disclosed plaque-disclosants meet some of the above criteria, but not all. Erythrosine, or FD&C Red No. 3, a currently popularly used water-soluble disclosing dye, has the disadvantage of unpleasant taste, non-discriminatory staining of the gingival tissues, and difficulty of removal from gingival tissues and oral surfaces. Although FD&C Red No. 3 has been widely used, its safety has been called into question and has been prohibited for use in cosmetic products in the United States as of Aug. 29, 1989.

It has been found that FD&C Red No. 40, also known as Allura Red, a water-soluble dye, has the desired attributes of an ideal plaque disclosing agent. This non-toxic dye provides a strong color intensity to the disclosed plaque, which is observable by the naked eye at visible light wavelengths, providing a sharp contrast between the disclosed plaque and surrounding soft and hard oral tissues; is water-soluble so that excess may be substantially rinsed out of the mouth and off of sink surfaces; and is more palatable to the taste than other commonly used disclosing dyes.

DESCRIPTION OF THE INVENTION

It is an object of the invention to provide a plaque-disclosing means which selectively stains plaque formed on all tooth surfaces, thus making plaque easily visible to the naked eye, at visible light wavelengths, without unduly staining surrounding soft and hard oral tissues and sink surfaces.

Another object of this invention is to provide an improved plaque-disclosing composition which rinses off easily.

Still another object of this invention is to provide a pleasant tasting non-toxic plaque-disclosing composition.

Other objects of this invention will become obvious to those skilled in the art upon reading the following specification.

These objects, and other objects of the present invention as hereinafter will become more readily apparent, can be obtained through the use of FD & C Red No. 40 as a plaque-disclosing agent. An embodiment of this invention comprises oral compositions in the form of a mouthrinse, dentifrice, aerosol spray, chewing gum, chewable tablet, wafer or lozenge, making dental plaque observable to the naked eye at visible wavelengths of light comprising 0.05 to 10% FD&C Red No. 40, wherein when said oral compositions are in solution form, said compositions comprise a liquid vehicle having up to 55% of a mono, di, or polyhydroxy compound. A further embodiment of this invention comprises a method of making dental plaque observable to the naked eye at visible wavelengths of light comprising introducing FD&C Red No. 40 dye into the oral cavity in an amount effective to disclose plaque and contacting said dye with the teeth in said oral cavity thereby staining any dental plaque present on said teeth.

FD & C Red No. 40, or Allura Red, (the disodium salt of 6-hydroxy-5-[(2-methoxy-5-methyl-4-sulfophenyl)azo]-2 naphthalenesulfonic acid)

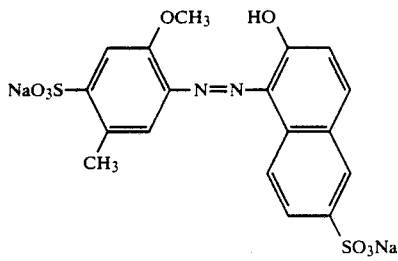

renders plaque on the teeth visible to the naked eye immediately upon contact therewith (i.e. brushing or rinsing or chewing), without excessively staining the gingival or other adjacent oral tissues and rinses off easily, both from oral tissue and sink surfaces. This selective staining is coupled with a more pleasant taste.

FD&C Red No. 40 was compared to two common non-toxic water-soluble plaque-disclosing dyes, F D & C Red No. 3 (erythrosine) and D&C Red No. 22 (eocine) (Table 1). A taste comparison of solutions of these three dyes demonstrates that FD&C Red No. 40 is more palatable i.e. less bitter tasting than either erythrosine or eocine. Further it was found that under visible light conditions FD&C Red No. 40 provides the most intense color of the dyed plaque, thus the greatest contrast between the disclosed plaque and adjacent oral tissues. A high contrast is of particular utility in detecting plaque in areas that are not readily observable such as the low lit posterior areas of the mouth and between the teeth. It should be noted that it is these precise areas which are the most prevalent sites of caries and periodontal disease.

It is particularly surprising that the color intensity of the FD&C Red No. 40 disclosed plaque was greater than the plaque disclosed by the other two dyes, as the FD&C Red No. 40 was much more easily rinsed off from the oral tissue and sink surfaces. This may indicate that FD&C Red No. 40 has a high affinity for plaque while exhibiting a low affinity for oral tissue and sink surfaces.

TABLE 1

| | Intensity* of Plaque Disclosing Dyes | | |
|---|---|---|---|
| | FD&C RED#3[a] | FD&C RED#22[b] | FD&C RED#40[c] |
| After Use | | | |
| Taste (bitterness) | 2.5 | 3.5 | 0.5 |
| Disclosed Dental | | | |
| Plaque | 4.0 | 2.0 | 5.0 |
| Lip staining | 2.0 | 2.0 | 3.0 |
| Gum staining | 2.0 | 0.5 | 2.5 |
| Tongue staining | 4.0 | 3.5 | 3.5 |
| Sink staining | 2.5 | 2.0 | 2.0 |
| AFTER TAP WATER RINSE | | | |
| Lip staining | 1.5 | 2.0 | 1.0 |
| Gum staining | 2.0 | 0.5 | 0.0 |
| Tongue staining | 3.0 | 2.0 | 2.5 |
| Sink staining | 2.0 | 0.5 | 0.5 |
| AFTER BRUSH/TAP WATER RINSE | | | |
| Lip staining | 0.0 | 1.5 | 0.0 |
| Gum staining | 0.0 | 0.0 | 0.0 |
| Tongue staining | 2.5 | 1.5 | 0.5 |
| Toothbrush staining | 1.0 | 0.0 | 0.0 |
| Sink staining | 1.5 | 0.5 | 0.0 |

[a] 0.25% solution
[b] 0.25% solution
[c] 1.00% solution
*intensity scale of 0–6,
0 = none
3 = moderate
6 = severe Upon excitation at visible light wavelengths (400–700 nm) aqueous solutions of FD&C Red No. 40 have an absorption maximum at 502 nm (absortivity=54 L/g-cm).

Other potential plaque-disclosing agents such as FD&C Blue No.1, FD&C Blue No. 2, D&C Green No. 5, and a mixture of FD&C Blue No. 1 and FD&C Yellow No. 5 have also been investigated. The color intensities of the disclosed plaque in each case were all much weaker than that of FD&C Red No. 40; thus these dyes were found not as suitable for use as plaque-disclosing agents.

Accordingly, the present invention relates to dental plaque disclosing compositions, making dental plaque observable to the naked eye at visible wavelengths, comprising an effective staining amount of FD&C Red No. 40 in a physiologically acceptable vehicle, which may be in the form of a solution, aerosol spray, gel, powder, chewing gum, chewable tablet, wafer or lozenge and the like.

The plaque-disclosing vehicle preferably constitutes a major amount of a physiologically acceptable inert carrier or diluent for the dye which is preferably tasteless or pleasant tasting; or an aqueous solution thereof, depending on the final form of the disclosing composition. More specifically, tablets, chewing gum, or powder contain substantially no water, whereas a liquid concentrate or rinse composition comprises an aqueous solution thereof. The carrier functions to facilitate the distribution of the dye in the oral cavity and to aid in the penetration of the dye onto plaque deposits. The concentration of FD&C Red No. 40, may vary from about 0.05 up to 10%, preferably 0.05 to 5%, most preferably 0.05 to 1.0% in the plaque-disclosing vehicle. Preferably, oral compositions in solution form, for example, mouthrinses and aerosol sprays, contain a liquid vehicle comprising up to 55% of a mono, di, or polyhydroxy compound.

A mouthrinse may be prepared by mixing a non-toxic alcohol and water vehicle with flavoring oil, surfactant, humectant, sweetener, color and optionally fluoride and/or an antibacterial antiplaque agent, for example, cetyl pyridinium chloride, benzethonium chloride, and chlorhexidine.

The alcohol component of a mouthwash, typically present in an amount of about 3–25% by weight, is a non-toxic alcohol such as isopropanol or ethanol, preferably utilizing denaturing components which also function as flavoring agents. These flavoring agents are used in an amount between about 0.02% to 2% of the total alcohol content of the mouthwash. Water typically comprises at least about 50% by weight of a mouthrinse and humectant about 5–40% by weight. Generally, the ratio of water to alcohol is in the range of from about 1:1 to about 20:1 preferably from 3:1 to 20:1 and most preferably from about 5:1 to 10:1 by weight.

The total amount of water-alcohol mixture in this type of preparation is typically in the range of from about 70 to about 99.9% by weight of the preparation.

The mouthwash may also contain 0.5 to 5% of a water-soluble organic surfactant, typically an anionic, cationic or amphoteric surfactant such as betaine, and most preferably a nonionic surfactant. Preferable nonionic surfactants include condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate), and most preferably polypropyleneoxide (e.g. Pluronic (trademark of BASF Wyandotte) materials).

Examples of mouthwash formulations which may be employed in the method of the present invention are as follows:

|  | parts by weight |
|---|---|
| ethyl alcohol | 10.0 |
| glycerol | 10.0 |
| flavor | 0.4 |
| sodium saccharin | 0.03 |
| nonionic surfactant | 2.0 |
| FD&C Red No. 40 | .05 to 1.0 |
| water | Q.S. to 100 |

The plaque-disclosing agent of this invention can also be incorporated in lozenges or in chewing gum or other products, e.g. by stirring into a warm gum base or coating the outer surface of a gum base; illustrative of which may be mentioned jelutong, rubber latex, vinylite resins, etc., desirably with conventional filler materials such as plasticizers or softeners, sugar or other sweeteners or carbohydrates such as glucose, sorbitol, sorbitol syrup, mannitol, xylitol, hydrogenated starch hydrolysate, and the like, and artificial sweeteners, saccharin salts, acesulfame-K and the like, and the free acid form of saccharin, and protein based sweeteners such as thaumatin.

A typical chewing gum may contain the following ingredients, in percent by weight based on the weight of the total gum formulation:

| Ingredients | parts by weight |
|---|---|
| Gum base | 10–40 |
| Sucrose | 50–75 |
| Corn syrup or Glucose | 10–20 |
| FD&C Red No. 40 | 0.05 to 1.0 |
| Flavor | 0.1–5 |

An alternate chewing gum formulation is as follows:

| Ingredients | parts by weight |
|---|---|
| Gum base | 10–50 |
| Binder | 3–10 |
| Filler (Sorbitol, mannitol or Combinaton thereof) | 5–80 |
| FD&C Red No. 40 | 0.05 to 1.0 |
| Flavor | 0.1–5 |

In certain sugarless gums, there is used as the binder ingredient a solution of sorbitol in water containing from about 10% to about 80%, preferably from about 50% to about 75% by weight of sorbitol in H$_2$O. In others, there is used a gum acacia-in-water system containing from about 30% to about 60%, preferably from about 45% to about 50% by weight of gum acacia powder.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutyleneisoprene copolymer, paraffin, petroleum wax, polyethylene, polyisobutylene, polyvinylacetate, etc.

A variety of traditional ingredients may be incorporated in the gum base, such as plasticizers or softeners. Examples of these ingredients include lanolin, stearic acid, sodium stearate, potassium stearate, glyceryl triacetate, glycerine, lecithin, glyceryl monostearate and the like. Natural waxes, petroleum waxes, polyurethane waxes, paraffin waxes and microcrystalline waxes may also be incorporated into the gum base to obtain a variety of desirable textures and consistency properties. Mixtures of these traditional ingredients are also contemplated. These traditional ingredients are generally employed in amounts of up to about 30% by weight, and preferably, in amounts of from about 3% to about 20% by weight of the final chewing gum product.

Mineral fillers may include aluminum hydroxide, alumina, aluminum silicate, titanium dioxide, talc, calcium carbonate, tricalcium phosphate, and mixtures thereof.

The flavoring which can be included in the chewing gum compositions made according to this invention can comprise one or more natural and/or synthetic flavors and/or oils derived from plants, leaves, flowers and fruit. Representative flavors and oils of these types include acids such as adipic, succinic and fumaric acid; citrus oils such as lemon oil, orange oil, lime oil and grapefruit oil; fruit essences, such as apple essence, pear essence, peach essence, strawberry essence, apricot essence, raspberry essence, cherry essence, plum essence and pineapple essence; essential oils such as peppermint oil, spearmint oil, bay oil, anise oil, oil of nutmeg, oil of sage, cassia oil and methylsalicylate (oil of wintergreen). Various synthetic flavors, such as those for a mixed fruit, may also be incorporated in the chewing gum with or without conventional preservatives.

The vehicle or carrier in a chewable tablet, or lozenge is a non-cariogenic solid water-soluble polyhydric alcohol (polyol) such an mannitol, xylitol, sorbitol, maltitol, a hydrogenated starch hydrolysate, for example Lycasin, hydrogenated disaccharides and hydrogenated polysaccharides, in an amount of about 90–98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations may contain about 2% gum as barrier agent to provide a shiny surface as opposed to a tablet which has a smooth finish. Suitable non-cariogenic gums include polycarboxylates such as Kappa carrageenan, carboxymethyl cellulose, hydroxyethyl cellulose, Gantrez and the like.

The lozenge or tablet may optionally be coated with a coating material such as wax, shellac, sodium carboxymethyl cellulose, polyethylene/maleic anhydride copolymer or kappa carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact with the active ingredients.

Examples of lozenge formulations which may be employed in the method of the present invention are as follows:

|  | parts by weight |
| --- | --- |
| Sorbitol | 75–98 |
| Corn Syrup | 1–20 |
| Flavor Oil | 0.1–1.0 |
| Tablet Lubricant | 0.1–5.0 |
| FD&C Red No. 40 | 0.05–1.0 |
| Water | 0.01–0.2 |

In certain other desirable forms of this invention, the plaque-disclosing composition may be substantially gel-like or paste-like in a dentifrice gel. The vehicle of such solid oral preparations in which the FD&C Red No. 40 dye is homogeneously distributed contains a liquid moiety of water and humectant and solid moiety of gelling agent together with a siliceous polishing agent having an empirical $SiO_2$ content of at least 70%, preferably 90%, a particle size in the range from 1 to 35 microns, preferably from 2 to 20 microns, substantially amorphous X-ray structure and an index of refraction between 1.44 and 1.47.

The proportion of the polishing agent of high silica content is in the range from 5% to 50% of the dentifrice, preferably from 10% to 30% such as from 15% to 25%. One abrasive is an amorphous alkali metal or alkaline earth metal aluminosilicate having a refractive index of from 1.44 to 1.47 and containing at least 70% silica, up to 10% alumina, up to 20% of moisture and up to 10% of sodium oxide. Typically, this material has a particle size in the range from 1 to 35 microns, preferably from 2 to 20 microns, e.g. 2 to 4 microns. The preferred moisture content is from 10% to 20% measured by ignition at 1000 degrees C. and the typical content of sodium oxide is from 5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 1 micron, a surface area of at least 200 $m^2/g$, preferably at least 300 $m^2/g$, and a bulk density of at least 0.15 $g/cm^3$, preferably at least 0.30$g/cm^3$, such as a dehydrated silica hydrogel (i.e. a xerogel), preferably of the well known regular density or intermediate density type. Examples of such amorphous silicic anhydride polishing agent are "Sylodent 700", "Syloid 63", "Syloid 72" and "Syloid 74" (SYLOID and SYLODENT are trademarks) which are described in "The Davison Family of Syloid Silicas" published by their manufacturer, W. R. Grace & Co., Davison Chemical Division and Zeodent 113 of J. M. Huber Corporation, Chemical Division Havre de Grace, Md. "Santocel 100" of Monsanto (SANTOCEL is a trade mark) is also a suitable dental abrasive. "Syloid 72"- has an average particle size of about 4 microns, a surface area of about 340 $m^2/g$ and a bulk density of about 1.77 $g/cm^3$. For "Syloid 63" the corresponding figures are about 9 microns, about 675 $m^2/g$ and about 0.4 $g/cm^3$. A grade of "Santocel 100" has a surface area of about 239 $m^2/g$ and a bulk density of about 0.24 $g/cm^3$. These amorphous silicic anhydrides may be used singly or in mixtures.

In the dentifrice, the liquid moiety may comprise water and humectant typically collectively in an amount ranging from about 10% to about 90% by weight of the preparation. Glycerine, polyethylene glycol (e.g. 400–600) and propylene glycol exemplify suitable humectants. Also advantageous are liquid mixtures of water, glycerine and sorbitol. In clear gels wherein the refractive index is an important consideration, about 10–30% by weight of water, 0 to about 80% by weight of glycerine, and about 20–80% by weight of sorbitol is preferably employed. In hazy or opacified gels, the water content is typically about 10–35% by weight and the humectant about 15–70% by weight.

The dentifrice gel further contains natural or synthetic gelling agent in proportions of about 0.1 to about 15, preferably about 0.1 to about 3 g by weight. Typical gelling agents include Irish moss, gum tragacanth, starch, polyvinylpyrrolidone, hydroxyethylpropylcellulose, hydroxybutyl methyl-cellulose, hydroxypropyl methyl cellulose, hydroxyethyl cellulose (e.g. available as Natrosol), iota carrageenan, sodium carboxymethyl cellulose as well as synthetic hectorite, a synthetic colloidal magnesium alkali metal silicate complex clay available for example as Laponite (e.g. CP, SP 2002,D) marketed by Laporte Industries Limited. Laponite D analysis shows, approximately by weight, 58.00% $SiO_2$, 25.40% MgO, 3.05% $Na_2O$, 0.98% $Li_2O$, and some water and tracer metals. Its true specific gravity is 2.53 and it has an apparent bulk density (g/ml. at 8% moisture) of 1.0.

Thickener, such as colloidal silica (e.g. the finely ground colloidal silica Syloid 244 or Sylodent 15) is preferably also present in the dentifrice gel vehicle, in amount of about 0.1-15% by weight, preferably about 1-12%, most preferably 12%.

When the oral composition is a dentifrice gel, it may be the entire composition or it may be present as a stripe in association with a separate portion of a dentifrice product.

Organic surface-active agents, such as those described with regard to mouthwashes may be present in an amount of about 0.5 to 5% by weight in the dentifrice compositions of the invention for increased prophylactic action, and to assist in achieving thorough and complete dispersion of the composition throughout the oral cavity. The organic surface-active agents typically may be anionic, nonionic or ampholytic in nature and it is preferred to employ as the surface-active agent a detersive material which imparts to the composition detersive and foaming properties. Anionic surfactants such as sodium lauryl sulfate are preferred in dentifrice compositions.

The plaque-disclosing agent of this invention may be incorporated into an aerosol spray. The aerosol spray may be prepared by mixing a non-toxic alcohol and water vehicle in which FD&C Red. No. 40 is solubilized. Preferably the non-toxic alcohol is not greater than 55% of the total solvent vehicle. Other water-soluble, non-toxic solvents such as glycerine and sorbitol can also be used. A non-toxic propellant system acts as a carrier of the plaque-disclosing formulation. Suitable propellants include those having a maximum heat of evaporation of about 50 B.t.u. per pound of total aerosol composition, to avoid causing pain to consumers subject to "cold-sensitivity" of the teeth. Among such propellants are $CClF_2CClF_2$, $CCl_2F_2$ and mixtures thereof. Optionally, the aerosol spray may comprise a surface active agent, preferably a nonionic surfactant, viscosity modifying agents, antifoams, sweeteners, and flavoring oils.

A typical aerosol spray formulation which may be employed in the method of the present invention is as follows:

|  | parts by weight |
| --- | --- |
| ethyl alcohol | 0–40.00 |
| deionized water | 35–90.00 |
| glycerine | 3.00 |
| propellant | .5–35 |
| FD&C Red. No. 40 | .05–1.0 |

Various other materials may be incorporated in the oral preparations of this invention such as whitening agents, preservatives, for example phenol, sodium benzoate, thymol, methyl salicylate, hexylresorcinol, silicones, chlorophyll compounds, anticalculus agents and/or ammonated materials such as urea diammonium phosphate, synthetic anionic linear polymeric polycarboxylates having a molecular weight of about 1000 to about 1,000,000, for example, Gantrez, or Luviform (manufactured by BASF Wyandotte, Parsippany, N.J.), sodium and potassium pyrophosphate, and mixtures thereof These adjuvants, where present, are incorporated in the preparations in amounts which do not substantially adversely affect the properties and characteristics desired.

Any suitable flavoring of sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, xylitol, sodium cyclamate, perillartine, APM(aspartyl phenyl alanine, methyl ester), sodium saccharine and the like. Suitably, flavor and sweetening agents may together comprise from about 0.1% to 5% more of the preparation.

The following examples are further illustrative of the nature of the present invention, but it is understood that the invention is not limited thereto. All amounts and proportions referred to herein and in the appended claims are by weight and temperatures are in degrees C unless otherwise indicated.

| Example 1 Mouthrinse | |
| --- | --- |
| Ingredient | Weight % |
| Ethyl Alcohol | 5.0 |
| Glycerin | 15.0 |
| Flavor | 0.08 |
| Sodium Saccharin | 0.01 |
| Pluronic F 108 | 1.0 |
| Pluronic F 127 | 1.0 |
| Sodium Benzoate | 0.5 |
| FD&C Red No. 40 | 1.0 |
| Water | Q.S. to 100 |

A mouthrinse composition is prepared according to Example 1. Pluronic F 108 and Pluronic F 127 are nonionic surfactant block copolymers of polyoxyethylene and polyoxypropylene. The mouthrinse is introduced into the oral cavity and mixed therethrough thereby making dental plaque visible to the naked eye.

| Example 2 Mouthrinse | |
| --- | --- |
| Ingredient | Weight % |
| Ethyl Alcohol | 12.5 |
| Glycerine | 10.0 |
| Flavor | .18 |
| Sodium Saccharin | .03 |
| Gantrez S-97 (13% A.I.) | 1.92 |
| Pentasodiumtripolyphosphate | .45 |
| Tetrapotassium pyrophosphate | 1.35 |
| Benzoic acid | .31 |
| Pluronic F 108 | 1.0 |
| Pluronic F 127 | 1.0 |
| Sodium fluoride | .02 |
| FD&C Red No. 40 | 1.0 |
| Water | Q.S. to 100 |

A mouthrinse composition is prepared according to Example 2 (Gantrez (trademark of GAF) is a pharmaceutical grade linear polymer carboxylate available from General Aniline & Film Corporation, New York, N.Y.). The mouthrinse is introduced into the oral cavity and mixed therethrough thereby making dental plaque visible to the naked eye.

| | Mouthrinse | |
| --- | --- | --- |
| Ingredient | Example 3 Weight % | Example 4 |
| Ethyl Alcohol | 12.5 | 12.5 |
| Glycerine | 10.0 | 10.0 |
| Flavor | .18 | .18 |
| Sodium Saccharin | .03 | .03 |
| Gantrez S-97 (13% Active) | 7.69 | 3.85 |
| Pluronic F 108 | 1.0 | 1.0 |
| Pluronic F 127 | 1.0 | 1.0 |
| Benzoate | 0.5 | 0.5 |
| FD&C Red No. 40 | .25 | .25 |
| Water | Q.S. to 100 | |

Mouthrinse compositions prepared according to Example 3 and 4 were adjusted to a pH of 6.0-7.0. These compositions exhibited a particularly high affinity for dental plaque.

| Example 5 Lozenge | |
| --- | --- |
| Ingredient | Weight % |
| Sorbitol | 97.2 |
| Corn Syrup | 2 |

Example 5
Lozenge

| Ingredient | Weight % |
| --- | --- |
| Flavor Oil | 0.5 |
| Magnesium Stearate | 0.15 |
| FD&C Red No. 40 | 0.06 |
| Water | q.s. to 100 |

A lozenge composition is prepared according to Example 5. The lozenge is introduced into the oral cavity and dissolved there, thereby making dental plaque visible to the naked eye.

Example 6
Chewing Gum

| Ingredients | Parts by weight |
| --- | --- |
| Gum Base | 30.0 |
| Sorbitol | 42.5 |
| Mannitol | 4.0 |
| 70% Sorbitol in $H_2O$ | 16.5 |
| Glycerin | 5.0 |
| FD&C Red No. 40 | 0.05 |
| Flavoring | 1.95 |
|  | 100 |

A chewing gum composition is prepared according to Example 6. The chewing gum composition is introduced into the oral cavity and masticated thereby making dental plaque visible to the naked eye.

Example 7
Chewing Gum

| Ingredients | parts by weight |
| --- | --- |
| Gum Base | 25.00 |
| Lecithin | .5 |
| Softeners | 9.6 |
| Mannitol | 15.30 |
| Flavor | 2.6 |
| FD&C Red No. 40 | 0.05 |
| Sorbitol | 46.95 |
|  | 100.00 |

A chewing gum composition is prepared according to Example 7. The chewing gum composition is introduced into the oral cavity and masticated thereby making dental plaque visible to the naked eye.

Example 8
Dentifrice

| | Weight % |
| --- | --- |
| deionized water | 37.158 |
| glycerine | 25.000 |
| silicon dioxide | 21.500 |
| tetrasodium pyrophosphate | 6.000 |
| synthetic silica | 3.000 |
| sodium lauryl sulfate | 1.200 |
| flavor | 1.000 |
| gantrez | 1.000 |
| sodium hydroxide (50% solution) | 1.000 |
| Xanthan gum | 1.000 |
| sodium benzoate | 0.500 |
| titanium dioxide | 0.500 |
| sodium saccharin | 0.300 |
| NaF | .242 |
| FD&C Red No. 40 | .600 |
| | 100.000 |

What is claimed is:

1. A method of making dental plaque observable to the naked eye comprising contacting teeth having plaque adhered thereto with FD&C Red No. 40 dye in solution in a quantity effective, at a concentration of at least 0.05% by weight to stain said plaque and render said plaque visible at wave lengths of light visible to said naked eye, exposing the teeth to visible wavelengths of light, and then observing, with the naked eye, for any stained dental plaque, if present, on said teeth.

2. The method of claim 1 wherein said teeth are contacted with a composition comprising 0.05-10% by weight of said FD&C Red No. 40 dye.

3. The method of claim 2 wherein said composition further comprises water.

4. The method of claim 3 wherein said composition comprises at least about 50% by weight of said water.

5. The method of claim 3 wherein said composition comprises a mono, di, or polyhydroxy compound present in the quantity of up to 55% by weight.

6. The method of claim 5 wherein said composition comprises from about 3 to about 25% by weight of said mono, di, or polyhydroxy compound.

7. The method of claim 6 wherein said mono, di, or polyhydroxy compound comprises a non-toxic alcohol.

8. The method of claim 7 wherein said composition further comprises flavoring agents present in an amount of from about 0.02% to about 2% of the total alcohol content in said composition.

9. The method of claim 3 wherein said composition further comprises about 5–40% by weight of a humectant.

10. The method of claim 6 wherein the ratio of water to alcohol ranges from about 1-1 to about 20-1.

11. The method of claim 3 wherein said composition comprises 0.5 to about 5% of a water soluble organic surfactant.

* * * * *